United States Patent [19]

Diehl et al.

[11] Patent Number: 5,750,623
[45] Date of Patent: May 12, 1998

[54] HOT-MELT ADHESIVES FOR DISPOSABLE ITEMS AND ARTICLES MADE THEREFROM

[75] Inventors: Charles F. Diehl; Jean M. Tancrede, both of Baton Rouge, La.

[73] Assignees: The Dow Chemical Co.; Exxon Chemical Patents, Inc., both of Del.

[21] Appl. No.: 650,734

[22] Filed: May 20, 1996

[51] Int. Cl.$^6$ .................... C08L 9/06; C08L 53/02
[52] U.S. Cl. .................... 525/98; 525/89; 525/95; 525/99
[58] Field of Search ............ 524/271, 274, 524/499; 525/93, 97, 98, 99, 89, 95

[56] References Cited

U.S. PATENT DOCUMENTS

| | | | |
|---|---|---|---|
| 3,239,478 | 3/1966 | Harlan, Jr. | 260/27 |
| 3,265,765 | 8/1966 | Holden et al. | 260/876 |
| 3,614,836 | 10/1971 | Snyder et al. | 525/98 |
| 3,917,607 | 11/1975 | Crossland et al. | 260/28.5 |
| 3,935,338 | 1/1976 | Robertson | 427/207 |
| 3,954,692 | 5/1976 | Downey | 260/33.6 |
| 4,104,327 | 8/1978 | Inoue et al. | 260/876 |
| 4,133,731 | 1/1979 | Hansen et al. | 204/159.17 |
| 4,151,057 | 4/1979 | St. Clair et al. | 204/159.17 |
| 4,152,231 | 5/1979 | St. Clair et al. | 204/159.17 |
| 4,163,764 | 8/1979 | Nash | 525/2 |
| 4,172,860 | 10/1979 | Feeney et al. | 525/97 |
| 4,259,220 | 3/1981 | Bunnelle et al. | 260/27 |
| 4,288,567 | 9/1981 | Feeney et al. | 525/99 |
| 4,302,371 | 11/1981 | Matsuo et al. | 260/28.5 |
| 4,419,494 | 12/1983 | Puletti et al. | 525/95 |
| 4,526,577 | 7/1985 | Schmidt, Jr. et al. | 604/366 |
| 4,556,464 | 12/1985 | St. Clair | 204/159.15 |
| 4,578,302 | 3/1986 | Schmidt, Jr. et al. | 428/110 |
| 4,660,858 | 4/1987 | Flanagan | 281/21 R |
| 4,699,938 | 10/1987 | Minamizaki et al. | 524/271 |
| 4,761,341 | 8/1988 | Rosiak et al. | 428/512 |
| 4,780,367 | 10/1988 | Lau et al. | 428/355 |
| 4,835,200 | 5/1989 | St. Clair | 524/100 |
| 4,944,993 | 7/1990 | Raykovitz et al. | 428/290 |
| 5,028,646 | 7/1991 | Miller et al. | 524/77 |
| 5,037,411 | 8/1991 | Malcolm et al. | 604/358 |
| 5,057,571 | 10/1991 | Malcolm et al. | 524/505 |
| 5,089,550 | 2/1992 | Sakagami et al. | 525/314 |
| 5,118,762 | 6/1992 | Chin | 525/314 |
| 5,143,968 | 9/1992 | Diehl et al. | 524/534 |
| 5,149,741 | 9/1992 | Alper et al. | 525/95 |
| 5,194,500 | 3/1993 | Chin et al. | 525/97 |
| 5,242,984 | 9/1993 | Dillman et al. | 525/314 |
| 5,266,394 | 11/1993 | Diehl et al. | 428/261 |
| 5,292,806 | 3/1994 | Diehl et al. | 525/89 |
| 5,292,819 | 3/1994 | Diehl et al. | 525/314 |
| 5,358,783 | 10/1994 | Diehl et al. | 428/344 |
| 5,372,870 | 12/1994 | Diehl et al. | 428/198 |
| 5,399,627 | 3/1995 | Diehl et al. | 525/314 |
| 5,412,032 | 5/1995 | Hansen et al. | 525/98 |

FOREIGN PATENT DOCUMENTS

| | | | |
|---|---|---|---|
| 0189485 | 8/1988 | Japan | 524/499 |

*Primary Examiner*—Peter A. Szekely
*Attorney, Agent, or Firm*—Pravel, Hewitt, Kimball & Krieger

[57] ABSTRACT

Hot-melt adhesive compositions containing high molecular weight linear styrene-isoprene-styrene block copolymers or high molecular weight linear styrene-butadiene-styrene copolymers, having little or no residual diblock, and articles made therefrom. The resulting adhesive composition may include solid tackifying and liquid tackifying resins.

15 Claims, No Drawings

HOT-MELT ADHESIVES FOR DISPOSABLE ITEMS AND ARTICLES MADE THEREFROM

BACKGROUND OF THE INVENTION:

1. Field Of The Invention:

The present invention relates to hot-melt adhesives (HMA) used in the construction of disposable articles. More particularly, the present invention relates to a hot-melt adhesive formulation containing a high molecular weight linear styrene-isoprene-styrene (SIS) block copolymer or a high molecular weight linear styrene-butadiene-styrene (SBS) copolymer with each of the copolymers having a minimum polystyrene block molecular weight of 18,000. Further, the linear SIS and SBS copolymers are preferably prepared in a sequential polymerization process which produces little or no residual diblock. The SIS or SBS block copolymers are combined with a solid tackifying resin and optionally a liquid tackifier resin or plasticizer oil to produce a hot-melt adhesive. Further, the invention relates to the construction of disposable articles wherein the novel hot-melt adhesive formulation is employed to bond a polyethylene or polypropylene substrate to a tissue, or non-woven fabric, or to attach an elastic band to a tissue or non-woven fabric.

2. General Background:

The preparation of hot-melt adhesive compositions from SIS block copolymers and SBS block copolymers is quite well known in the art. Because of the various characteristics that accompany the success of hot-melt adhesives, some hot-melt adhesives may be useful in one particular application, where as another may be useful in a second application. Additionally, some applications of hot-melt adhesives of block copolymers may require bonding between substrate formed of different materials, such as plastics or the like. In the line of disposable articles, for example, disposable diapers, sanitary napkins, bed pads, etc., such articles of manufacture usually require the use of a hot-melt adhesive which may adhere at a relatively low temperature in order to avoid damage to one of the other substrates in the disposable article.

For example, in disposable articles such as diapers or the like, the hot-melt adhesive must be capable of bonding a non-woven moisture absorbent fabric through a continuous or discontinuous film to a substrate in order to bond the non-woven fabric thereto. Furthermore, in disposable diapers, a non-woven fabric is generally bonded to an inner ply of a soft material for core stabilization. The hot-melt adhesive would be utilized between the outer ply of moisture impervious material and to the soft surface material so as to minimize moisture.

In the construction of such disposable articles, which may be constructed by applying the hot-melt adhesive through extrusion, spray or multi-line type techniques, one of several formulating approaches have typically been practiced in the art. A first method would be to provide a relatively low molecular weight linear styrene-isoprene-styrene or styrene-butadiene-styrene copolymer in combination with a tackifier resin and oil in formulations which would usually contain 15 to 35 wt percent of the block copolymer. One example of this combination is disclosed in U.S. Pat. No. 5,149,741, where a multipurpose adhesive composition for a hot-melt adhesive contains about twenty five parts by weight of an SIS block copolymer containing 25% styrene, by weight, of the entire block copolymer; about 60 parts of a pentaerythritol ester; about 15 parts by weight of a naphthenic/paraffinic mineral oil; and 0.1 to 2.0 parts by weight of a blend of phosphite antioxidant, a hindered phenolic antioxidant and a thioester synergist, respectively. In this combination, the SIS copolymers have as a percentage of the total weight of the copolymers a styrene content in the range of 25–50%, with the SIS copolymer being of relatively low molecular weight. In addition, the adhesive compositions described contain 15–40 wt % of the SIS.

The second approach would be the use of a relatively high molecular weight radial or multi-arm styrene-butadiene or styrene-isoprene block copolymer having the formula: (A—B)n—Y wherein Y is a multivalent coupling agent, A comprises a polyvinyl substituted aromatic block (e.g. styrene), B comprises a polymeric rubbery midblock (e.g. isoprene or butadiene) and n is an integer of at least 3, used in combination with tackifier resins and oil, in a hot-melt adhesive formulation which would contain only 5 to 14 weight percent of the block copolymer. The advantage of this approach, which is disclosed in U.S. Pat. No. 5,057,571, for example, is that it results in a lower hot-melt adhesive formulation cost due to the lower level of block copolymer employed, which is the most expensive ingredient in a hot-melt adhesive compound. As disclosed in the '571 patent, it was found that a low level of radial block copolymer having a molecular weight of greater than about 140,000 and preferably greater than 160,000, could be utilized to obtain the qualities required in a hot-melt adhesive, by having 5–14% of the radial block copolymer of the molecular weight described above.

U.S. Pat. No. 5,037,411, entitled "Disposable Article Multi-Line Construction Adhesive", assigned to H. B. Fuller Company, also discloses a disposable article utilizing a hot-melt pressure sensitive adhesive composition which would include 5–15% by weight of a radial copolymer, together with a compatible tackifying resin, plasticizing oil, petroleum derived wax and a stabilizer. In one example cited in the '411 patent, Table 4 compared adhesive prepared with a high molecular weight radial block copolymer as taught in the invention, and adhesives prepared from a linear multi-block A—B—A—B—A—B copolymer. The data, as indicated in the patent, clearly show that the adhesives made with the radial copolymer at levels of 15% and less are different and superior to conventional adhesives with greater than 15 wt % polymer in the adhesive formulation.

However, there remains a need for an improved hot-melt adhesive composition which would be useful in the assembly of disposable articles such as diapers, bed pads and feminine care pads, which would utilize a combination of a very high molecular weight linear SIS or SBS block copolymer yet at a rather low level of combination, that is, less than 15 weight percent of the block polymer in the hot-melt adhesive formulation, allowing a low rubber formulation compared to conventional hot-melt adhesives based on low molecular weight linear SIS and SBS block copolymers.

It is therefore a primary object of the present invention to fulfill these needs and others.

A particular object of this invention is to provide a novel high molecular weight linear A—B—A where A is a polystyrene block and B is a rubbery conjugated diene block (e.g. isoprene or butadiene) block co-polymer, in an improved hot-melt adhesive combination which is useful in the assembly of disposable articles, particularly those articles of multi-line construction.

It is a further object of the present invention to provide a hot-melt adhesive composition which utilizes a very low level of high molecular weight linear block copolymer which has superior heat resistance, superior static time to failure with low viscosity, good peel adhesion, good tack and high ability for bonding to a polyethylene or polypropylene substrate at the temperature below that which would be injurious to the substrate.

A further and yet more specific object is to provide disposable articles, particularly articles of multi-line construction such as diapers, bed pads and feminine care pads, wherein a polyethylene or polypropylene substrate is bonded to a tissue, or non-woven polyethylene or polypropylene substrate, or both, via the use of said improved hot-melt adhesive compositions.

It is a further, yet more specific object of the present invention to provide an improved hot-melt adhesive composition, which would allow a low-cost product, due to the use of a substantially low amount of the high molecular weight linear block copolymer in the HMA formulation.

In a preferred embodiment of the present invention the high molecular weight linear SIS and SBS copolymers are produced via a sequential polymerization process (A—B—A sequentially polymerized), such that the final copolymer product contains little to no residual diblock.

THE INVENTION

Block Copolymer Polymerization Process

As is well known, polymers containing both aromatic and ethylenic unsaturation can be prepared by copolymerizing one or more polyolefins, particularly a diolefin, in this case isoprene or butadiene, with one or more alkenyl aromatic hydrocarbon monomers, in this case styrene. The copolymer may, or course, be random, tapered, block or a combination of these, in this case block. The blocks in the copolymers of this invention are linear.

Polymers containing ethylenic unsaturation or both aromatic and ethylenic unsaturation may be prepared using free-radical, cationic and anionic initiators or polymerization catalysts. Such polymers may be prepared using bulk, solution or emulsion techniques. In any case, the polymer containing at least ethylenic unsaturation will, generally, be recovered as a solid such as a crumb, a powder, a pellet or the like. Polymers containing ethylenic unsaturation and polymers containing both aromatic and ethylenic unsaturation are, of course, available commercially from several suppliers.

Polymers of conjugated diolefins and copolymers of one or more conjugated diolefins and one or more alkenyl aromatic hydrocarbon monomers such as predominantly liners S—I—S or S—B—S block copolymers are frequently prepared in solution using anionic polymerization techniques. In general, when solution anionic techniques are used, these S—I—S or S—B—S block copolymers are prepared by contacting the monomers to be polymerized simultaneously or sequentially with an organoalkali metal compound in a suitable solvent at a temperature within the range from about 150° C. to about 300° C., preferably at a temperature within the range from about 0° C. to about 100° C. Particularly effective anionic polymerization initiators are organolithium compounds having the general formula:

$$RLi_n$$

Wherein:

R is an aliphatic, cycloaliphatic, aromatic or alkyl-substituted aromatic hydrocarbon radical having from 1 to about 20 carbon atoms; and n is an integer of 1 to 4.

In general, any of the solvents known in the prior art to be useful in the preparation of such polymers may be used. Suitable solvents, then, include straight- and branched-chain hydrocarbons such as pentane, hexane, heptane, octane and the like, as well as alkyl-substituted derivatives thereof; cycloaliphatic hydrocarbons such as cyclopentane, cyclohexane, cycloheptane and the like, as well as, alkyl-substituted derivatives thereof; aromatic and alkyl-substituted aromatic hydrocarbons such as benzene, naphthalene, toluene, zylene and the like; hydrogenated aromatic hydrocarbons such as tetralin, decalin and the like; linear and cyclic ethers such as methyl ether, methyl ethyl ether, tetrahydrofuran and the like.

The concentration of the initiator can be regulated to control the molecular weight of the overall composition and of the polystyrene blocks. Generally, the initiator concentration is in the range of about 0.25 to about 50 millimoles per 100 grams of monomer. The ratio of the initiator to the monomer determines the block size, i.e. the higher the ratio of initiator to monomer the smaller the molecular weight of the block.

Methods of controlling the molecular weights of the blocks and the overall polymer are quite well known. For instance, such are disclosed in U.S. Pat. Nos. 3,149,182, which states that amount of monomer can be kept constant and different molecular weights can be achieved by changing the amount of organolithium iniator, or the amount of initiator catalyst can be kept constant and different molecular weights can be achieved by varying the amount of the monomer, and in U.S. Pat. No. 3,231,635, the disclosures of which are herein incorporated by reference, and many others.

The first step of the process involves contacting the monoalkenyl arene and the organomonolithium compound (initiator) in the presence of an inert diluent therein forming a living polymer compound having the simplified structure A—Li. The monoalkenyl arene is preferably styrene.

Next, the living polymer in solution is contacted with a conjugated diene. Preferred dienes include butadiene and isoprene. The resulting living polymer has a simplified structure A—B—Li.

At this point, one of two processes can be employed to produce a linear A—B—A triblock copolymer, i.e. (1) coupling process or (2) sequential process. In the coupling process, the living A—B—Li polymer is coupled with a multifunctional coupling agent.

There are a wide variety of coupling agents that can be employed. Any polyfunctional coupling agent which contains at least two reactive sites can be employed. Examples of the types of compounds which can be used include the polyepoxides, polyisocyanates, polyimines, polyaldehydes, polyketones, polyanhydrides, polyesters, polyhalides, and the like. These compounds can contain two or more types of functional groups such as the combination of epoxy and aldehyde groups, isocyanate and halide groups, and the like. Various other substituents which are inert in the treating reaction can be present such as hydrocarbon radicals as exemplified by the alkyl, cycloalkyl, aryl, aralkyl and alkaryl groups and the alkoxy, aryloxy, alkylthio, arylthio, and tertiary amino groups. Many suitable types of these polyfunctional compounds have been described in U.S. Pat. Nos. 3,595,941; 3,468,972; 3,135,716; 3,078,254; and 3,594,452. When the coupling agent has two reactive sites such as dibromoethane, the polymer will have a linear ABA structure. When the coupling agent has three or more reactive sites, such as silicon tetrachloride, the polymer will have a radial or branched structure, such as $(AB)_nBA$.

In the prior art, such as that exemplified by U.S. Pat. Nos. 3,595,941 and 3,468,972, the effort was always made to select the particular coupling agent or reaction conditions that resulted in the highest coupling efficiency. Coupling efficiency is defined as the number of molecules of coupled polymer divided by the number of molecules of coupled polymer plus the number of molecules of uncoupled polymer. Thus, when producing an SIS linear polymer, the coupling efficiency is shown by the following relationship:

$$\frac{\text{\# of molecules of } SIS}{\text{\# of molecules of } SIS \text{ plus } SI}$$

Coupling efficiency cain be determined theoretically from the stoichiometric quantity of coupling agent required for complete coupling, or coupling efficiency can be determined by an analytical method such as gel permeation chromotography. Typical prior art coupling efficiency is from about 80% to almost 100%.

The typical coupling conditions include a temperature of between about 65° C. and about 80° C., and sufficient pressure to maintain the reactants in a liquid phase.

Following the coupling reaction or when the desired coupling efficiency has been obtained, the product is neutralized such as by the addition of terminators, e.g. water, alcohol or other reagents, for the purpose of removing the lithium radical forming the nucleus for the condensed polymer product. The product is then recovered such as by coagulation utilizing hot water or steam or both, or by employing vacuum devolitilization/extrusion.

Alternatively, the living A—B—Li polymer can be reacted with a second addition of styrene monomer, in the sequential polymerization process, to produce a linear A—B—A triblock copolymer.

This process offers the advantage of leaving no measurable residual diblock.

Following the sequential polymerization, the product is terminated such as by the addition of a protic terminating agent, e.g. water, alcohol or other reagents or with hydrogen, for the purpose of removing the lithium radical forming the nucleus for the condensed polymer product. The product is then recovered such as by coagulation utilizing hot water or steam or both or by employing vacuum devolitilization/ extrusion. The polymers are not hydrogenated.

In a preferred embodiment of the present invention, the linear A—B—A block copolymers used herein contain more than 95% triblock. In the case where the A—B—A block copolymer is prepared using the coupling process described above, a preferred embodiment of the present invention employs an A—B—A block copolymer in which the coupling efficiency is greater than 95%. In the most preferred embodiment of the present invention, the linear A—B—A block copolymers used herein are sequentially polymerized, according to the sequential process described above, and contain greater than 98% triblock copolymer.

The hot-melt adhesive composition of the present invention is, in particular, comprised of 5 to 15 weight percent of a high molecular weight linear SIS or SBS block copolymer or mixtures thereof, said linear SIS block copolymer containing 25 to 35 weight percent styrene, and having a molecular weight of 120,000 to 200,000, which would be corrected for composition. The linear SBS block copolymer would contain 25 to 35 weight percent polystyrene, with a molecular weight of 100,000 to 180,000, also corrected for composition. Furthermore said linear SIS and SBS block copolymers have a minimum polystyrene block molecular weight of approximately 18,000. Further still, the linear SIS and SBS block copolymers would preferably be prepared in the sequential polymerization process described earlier and would contain very little or no residual diblock. Further, the linear SIS and SBS containing compositions would include 45 to 85 weight percent of a compatible solid tackifying resin, and 0–35 weight percent of a plasticizing oil or liquid tackifying resin.

Further still, the hot-melt adhesive would have about 5 to 15 percent, and more preferably about 8 to about 13 percent based on the weight of the hot melt adhesive composition, of a linear A—B—A block copolymer wherein the B component is polyisoprene; the A component is polystyrene, the average molecular weight, corrected for the composition of the polymer, of a polystyrene block is about 18,000 to 26,000 more preferably about 18,000 to 24,000 and most preferably about 18,000 to 22,000. The overall average molecular weight of the linear block co-polymer, corrected for the composition of the polymer would be about 120,000 to about 200,000 more preferably about 125,000 to 180,000 and most preferably about 125,000 to about 150,000 and wherein the A component is present in an amount of at least about 25 to 35, more preferably about 28 to about 32 parts per 100 parts by weight of the block copolymer; further having from about 45 percent to about 85 percent of a compatible solid tackifying resin, based on the weight of the hot melt composite; and from about 0 percent to about 35 percent of a plasticizing oil or liquid tackifying resin, based upon the weight of the hot melt adhesive.

Alternatively, the hot melt-adhesive would have about 5 to about 15 percent, most preferably about 8 to 13 percent based on the weight of the hot melt adhesive composition, of a linear A—B—A block copolymer where the B component is polybutadiene, the average molecular weight, corrected for the composition of the polymer, polystyrene block is about 18,000 to 26,000, more preferably 18,000 to 24,000 and most preferably 18,000 to 22,000, where the overall average molecular weight, corrected for the composition of the polymer, of the linear block copolymer is about 100,000 to 180,000, more preferably 110,000 to 160,000, and most preferably 110,000 to 140,000, and wherein the A component is present in an amount of at least 25 to 35 parts, more preferably 28 to 32 parts per 100 parts by weight of the block copolymer; further from about 45 percent to about 85 percent of a compatible solid tackifying resin, based on the weight of the hot-melt adhesive composition; and from about 0 percent to about 35 percent of a plasticizing oil or liquid tackifying resin; based upon the weights of the hot-melt adhesive.

The articles utilizing this novel hot-melt adhesive would be constructed by employing extrusion, spray, or multi-line type techniques for joining the layer to a substrate, or to join an elastic band to a substrate, the process as employed which is known in the art at this time.

The molecular weight reported herein is the molecular weight corrected for the composition of the polymer. Molecular weights quoted are not polystyrene equivalent molecular weight, but actual molecular weights which have been corrected for the composition of the polymer. The molecular weight was determined by gel permeation chromatography (GPC) using the methods described previously in the literature: J. R. Runyon, et. al., and J. Polym. Sci. 13, 2359 (1969). L. H. Tung, J. Appl. Polym. Sci. 24, 953–963 (1979).

These hot-melt adhesive compositions, constituted of an A—B—A block copolymer of relatively high overall molecular weight to which the primary tackifying resin, the secondary tackifying resin or plasticizing oil, and stabilizer have been added, have been found to possess properties which are admirably suitable for the construction of disposable articles, particularly disposable articles of multi-line construction wherein the adhesive is applied as fine parallel longitudinal strips, or as a multi-dot pattern of adhesive droplets, to bond together a moisture impervious outer polyethylene or polypropylene sheet and an inner moisture absorbent sheet, or tissue, as used in diaper constructions. These hot melt adhesive compositions can be melted, and maintained under a blanketing nitrogen atmosphere, at relatively low to high temperatures without thermal degradation. The compositions can be applied in fluid form to polyethylene and polypropylene substrates as continuous or discontinuous films, suitable as fine lines or as patterns of multidots, without any risk of damage to the polyethylene or polypropylene substrate. These hot-melt adhesive compositions have also been found to serve a construction function in binding together an outer sheet, or wrapper overlapped with an absorbent pad as required in the construction of sanitary napkins. The hot-melt adhesive composition applied as a fluid permeates the overlapped area to bind and seal the absorbent pad inside the outer sheet which serves as a wrapper.

Tackifying Resin

The primary tackifying resins useful in the practice of this invention include hydrocarbon resins, synthetic polyterpenes, resin esters and natural terpenes which are semi-solid or solid at ambient temperas, and soften or become liquid at temperatures ranging generally from about 40° C. to about 135° C., preferably from about 70° C. to about 120° C. Exemplary of the primary tackifying resins are compatible resins such as (1) natural and modified rosins such, for example, as gum rosin, wood rosin, tall oil rosin, distilled rosin, hydrogenated rosin, dimerized rosin, and polymerized rosin; (2) glycerol and pentaerythritol esters of natural and modified rosins such, for example, as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natured terpenes, e.g., styrene/erpene and alpha methyl styrene/terpene; (4) polyterpene resins having a softening point, as determined by ASTM method E28-58T, of from about 80°to 150° C.; the latter polyterpene resins generally resulting from the polymerization of terpene hydrocarbons, such as the bicylic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins having a Ball and Ring softening point of from about 40°to 135° C.; the latter resins resulting from the polymerization of monomers consisting primarily of olefins and diolefins; also included are the hydrogenated aliphatic petroleum hydrocarbon resins; (7) aromatic petroleum hydrocarbon resins, and mixed aromatic and aliphatic paraffin hydrocarbon resins, and the hydrogenated derivatives thereof; (8) aromatic modified alicyclic petroleum hydrocarbon resins and the hydrogenated derivatives thereof; and (9) alicyclic petroleum hydrocarbon resins and the hydrogenated derivatives thereof. The preferred primary tackifying resins for use in the practice of this invention are represented by sub-paragraphs (8) and (9) when the hot-melt adhesive is formulated using an SIS block copolymer and sub-paragraphs (2), (3), and (8), when the hot-melt adhesive is formulated using an SBS block copolymer.

Suitable secondary tackifying resins are those named species wherein the resin is a liquid at ambient temperature.

Plasticizer Oil

Various plasticizing oils are useful in the practice of this invention. The plasticizing oil can be used in place of or in combination with the secondary tackifier to reduce viscosity and improve tack properties. Plasticizing oils which have been found useful include olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less that 15% by weight of the oil). Alternately, the oil may be totally nonaromatic. The oilgomers may be polypropylenes, polybutenes, hydrogenated polyisoprene, hydrogenated polybutadiene, polypiperylene and copolymers of piperylene and isoprene, or the like having average molecular weights between about 350 and about 10,000. Vegetable and animal oils include glyceryl esters of the usual fatty acids and polymerization products thereof.

The stabilizer, or antioxidant, used in accordance with the practice of this invention includes high molecular weight hindered phenols and multifunctional phenols such as sulfur and phosphorous-containing phenols. Hindered phenols are well known to those skilled in the art and may be characterized as phenolic hydroxyl group thereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include: 1,3,5-trimethyl 2,4,6-tris (3,5-di-ter-butyl-4-hydroxybenzyl) benzene; pentae-rythrityl tetrakis-3 (3,5-di-tertbutyl-4-hydroxyphenyl) proprionate; n-octadecyl-3, 3,5-di-tert-butyl-4-hydroxy-phenyl)-propionate; 4,4'-methylenbis (2,6-tert-butyl-phenol); 4,4'-thiobis (6-tert-butyl-o-cresol); 2,6-di-tert-butylphenol; 6-(4-hydroxyphenoxy) -2,4-bis(n-octyl-thi-0)- 1,3,5 triazine: di-n-octadecyl 3,5-di-tert-butyl-4-hydroxy-benzylphosphonate; 2-(n-octylthio) ethyl 3,5-di-tert-butyl-4-hydroxy-benzoate; and sorbitol [hex 3-(3,5-di-tert-butyl-4-hydroxyphenyl)-propionate.]

The hot melt adhesive composition is prepared for use by blending the A—B—A block copolymer with the primary tackifying resin, the secondary tackifying resin or plasticizing oil, and stabilizer, in any order or sequence, or these materials can be added together simultaneously to form the adhesive composition. In commercial practice it would be expected that the primary tackifying resin and copolymer, with or without the simultaneous addition of the secondary tackifying resin or plasticizing oil, and stabilizer, would be blended together at sufficiently elevated temperature to form a fluid melt. For example, the copolymer can be blended with the solid compatible primary tackifying resin at temperatures ranging from about 110° C. to about 200° C., preferably at from about 130° C. to about 180° C. to form a fluid melt. The secondary liquid tackifying resin, or plasticizing oil, and stabilizer, can then be added to the melt. Alternatively, the fluid melt can be prepared with all components of the adhesive composition present ab initio.

In one embodiment of the preparation of the hot-melt adhesive as described above, adhesive of formulations were prepared in a sigma-blade hot-melt compounding batch mixer, the linear block copolymer was pre-mixed with the plasticizer oil at a level of 33 wt % oil, either by the technique of dry-blending, melt-compounding, or by solvent-blending in cyclohexane followed by vacuum devolatilization, in order to produce an oiled block copolymer. The hot-melt adhesive formulation consisted in general of the following (ECR 179A Tackifier resin (EXXON Chemical) refers to aromatic modified alicyclic petroleum hydrocarbon resins; Tufflo® 6056 Oil (Lyondell Petroleum) is commonly known and referred to as white oil or a plasticizing oil; and Irganox® 1010 Stabilizer (Ciba-Geigy) is an anti-oxidant and is one of the hindered phenols, examples of which are listed above under the heading Plasticizer Oil):

|  | wt. (g) |
|---|---|
| Oiled rubber (33 wt % oil) | 107.4 |
| ECR 179A Tackifier resin (EXXON Chemical) | 432 |
| Tufflo ® 6056 Oil (Lyondell Petroleum) | 132.6 |
| Irganox ® 1010 Stabilizer (Ciba-Geigy) | 1.5 |

In a preferred embodiment, after correcting for the oil content of the oiled block copolymer, the above formulation would contain the following wt % of the major ingredients: block copolymer/tackifier/oil=11 %/64%/25%. The melt mixer was then preheated to a temperature of 340 degrees fahrenheit. One-half of the tackifier resin and all of the Irganox 1010 was added, and this was allowed to mix for two minutes. All of the pre-oiled block copolymer was then added and mixing continued for 4.5 hrs. The remainder of the tackifier resin was added and mixing continued for an additional one hour. The oil was then added in 1/3 increments with 30 minutes of mixing following each addition. The polymer characterization and adhesive testing procedures have been described in U.S. Pat. Nos. 5,266,314 and 5,292,819 which are incorporated herein by reference.

In testing the adhesive tensile of the hot-melt adhesive formulation, a 0.062 inch thick slab of the HMA was compression molded in a chase between two sheets of release-coated paper, in a press at a temperature of 130° C. The molded slab of HMA was removed from the chase and excess paper and adhesive were removed. The samples were then conditioned under ASTM conditions (23+/–2 degrees C, 50+/–5% relative humidity) for 24 hours prior to testing. The tensile testing was conducted in accordance with ASTM D-412. Tensile dog bones were die-cut from the molded sheet, and then tested on a tensile tester using a gauge length of 1 inch and a cross-head speed of 12 inches/min. The ultimate tensile was calculated as the average measured on four different dog bones.

In Table 1, the results shown for example 7 & 8, contribute and establish an acceptable range for HMA performance as defined by the known prior art. Example 7 shows the results of a very high molecular weight radial $(SB)_n$ formulated at low rubber levels (11 wt %), similar to those levels as outlined in U.S. Pat. No. 5,037,411, granted to H. B. Fuller. Example 8, which is based on a higher rubber formulation (20 wt %) is representative of the results obtained for formulations like those as described in U.S. Pat. No. 4,526,577.

The results, as shown in Table 1, indicate that the very high molecular weight linear SBS of this invention, as seen in Examples 1 and 2, exhibit shear adhesive failure temperature (SAFT), peel, and HMA tensile properties that are equivalent or better than those of the prior art examples recited in Examples 7 & 8 in Table 1. In addition, it should be noted that the adhesive viscosities for Examples 1 and 2 are equivalent or lower than the prior art examples 7 & 8 in Table 1. Lower viscosities allow for ease in application at low temperatures.

It is also apparent that the results for Examples 4 & 6 are not acceptable. Each of these examples show very low SAFT, and Examples 4 & 6 also have very low adhesive tensile. These two SBS utilized are well below the molecular weight range defined by this invention. This explains their inferior performance. These low molecular SBS types will only produce acceptable HMA performance in higher rubber formulations in the amount of 15–35 wt % as taught in U.S. Pat. No. 4,526,577.

It is also apparent that Example 3 has inferior performance when compared to Examples 1 & 2 in Table 1. The linear coupled SBS used in Example 3 has sufficiently high molecular weight of 125,000, however, it also contains 21.3 wt % residual uncoupled diblock. The residual diblock is responsible for the lower SAFT and HMA tensile values. This demonstrates that low diblock SBS polymers produced by a sequential polymerization process produce superior results in the formulations of this invention.

In the high molecular weight linear SIS, examples 9, 10, 11, and 12 SAFT and HMA tensile performance increase with increased molecular weight and each of these exhibits performance equivalent to or better than that of the prior art examples 7 and 8. Example 13, which is high molecular weight linear coupled SIS, illustrates the detrimental effect of residual uncoupled diblock.

Example 14 is too low in molecular weight and therefore is deficient in performance (SAFT). This polymer would only have acceptable performance in a formulation containing greater than 15% rubber.

Example 15 has sufficiently high molecular weight (MW), but due to its low styrene content and the resulting low polystyrene block MW, it exhibits very low SAFT and HMA tensile.

EXAMPLE 1

To a 5-gallon stirred reactor under a nitrogen atmosphere were added 12.3 kg of cyclohexane solvent and 106.3 g of a 0.125 M solution of sec-butyl lithium in cyclohexane. The temperature of the reactor was brought to 76° C. and 301.4 g of styrene monomer was added. Polymerization of the styrene was allowed to continue for 36 min. The reaction mixture was cooled to 62° C. and 1406.4 g of butadiene monomer was added. The butadiene was allowed to polymerize for 45 minutes, during which the reaction temperature reached a maximum of 91.2° C. At the end of the 45 minutes, an additional 301.4 g of styrene monomer was added. The reaction was allowed to continue for another 30 minutes before the reaction was terminated by the addition of an excess of isopropanol to the polymer solution. Following the addition of an antioxidant package consisting of a hindered phenol and tris-nonylphenylphosphite (TNPP), the polymer was recovered from solution by devolatilization in a vacuum oven under nitrogen at 100° C. for 3 hrs. The resulting sequentially polymerized linear SBS polymer had a styrene content of 31.1 wt % and a molecular weight (corrected for composition) of 124,700. There was no detectable amount of styrene butadiene diblock.

EXAMPLE 2

This combination was prepared according to the same general procedure outlined in Example 1, with the exception of slightly different weights of sec-butyl lithium and styrene and butadiene monomers. The resulting sequentially polymerized linear SBS had a styrene content of 31.0 wt % and a molecular weight (corrected for composition) of 117,770. There was no detectable amount of SB diblock.

EXAMPLE 3

To a 5-gallon stirred reactor under a nitrogen atmosphere were added 12.3 kg of cyclohexane solvent and 299.4 g of a 0.125 M solution of sec-butyl lithium in cyclohexane. The temperature of the reactor was brought to 75° C. and 589.7 g of styrene monomer was added. Polymerization of the styrene was allowed to continue for 45 min. The reaction mixture was cooled to 59° C. and 1409.4 g of butadiene monomer was added. The butadiene was allowed to polymerize for 65 minutes, during which the reaction temperature reached a maximum of 107° C. At the end of the 65 minutes, the temperature had dropped to 50° C. and 43.3 g of a 1.065 M solution of dibromoethane coupling agent in cyclohexane was added to the reactor. The coupling reaction was allowed to continue for 40 minutes before being terminated by the addition of an excess of isopropanol to the polymer solution. Following the addition of an antioxidant package consisting of a hindered phenol and tris-nonylphenylphosphite (TNPP), the polymer was recovered from solution by devolatilization in a vacuum under nitrogen at 100° C. for 3 hrs. The resulting coupled linear SBS polymer had a styrene content of 31.1 wt % and a molecular weight (corrected for composition) of 124,700. The product also contained 21.3 wt % of residual uncoupled SB diblock.

EXAMPLES 4 & 5

Examples 4 & 5 are sequentially polymerized linear SBS polymers that are commercially available from DEXCO Polymers. Their properties are described in Table 1. These SBS polymers are representative of the types employed in the formulations described in U.S. Pat. No. 4,526,577.

EXAMPLES 6 & 8

Examples 6 & 8 are a linear multiblock (tapered) SBS polymer which is commercially available from Firestone. This product is the principal example employed in the formulations described in U.S. Pat. No. 4,526,577. In example 6, this polymer was formulated at 11 wt % rubber, while in example 8 it was formulated at 20 wt % rubber.

EXAMPLE 7

Example 7 is a high molecular weight radial (SB)n polymer representative of the type employed in the formulations described in U.S. Pat. No. 5,037,411.

EXAMPLE 9

To a 5-gallon stirred reactor under a nitrogen atmosphere were added 12.4 kg of cyclohexane solvent and 144.6 g of a 0.125 M solution of sec-butyl lithium in cyclohexane. The temperature of the reactor was brought to 79° C. and 298.5 g of styrene monomer was added. Polymerization of the styrene was allowed to continue for 60 min. The reaction mixture was cooled to 61° C. and 1426.9 g of isoprene monomer was added. The isoprene was allowed to polymerize for 55 minutes, during which the reaction temperature reached a maximum of 98° C. At the end of the 55 minutes, an additional 298.5 g of styrene monomer was added. The reaction was allowed to continue for another 30 minutes before the reaction was terminated by the addition of an excess of isopropanol to the polymer solution. Following the addition of an antioxidant package consisting of a hindered phenol and tris-nonylphenylphosphite (TNPP), the polymer was recovered from solution by devolatilization in a vacuum over under nitrogen at 100° C. for 3 hrs. The resulting sequentially polymerized linear SIS polymer had a styrene content of 30.8 wt % and a molecular weight (corrected for composition) of 120,000. There was no detectable amount of styrene-isoprene (SI) diblock.

EXAMPLES 10, 11, 12

Examples 10-12 were prepared according to the same general procedure outlined in Example 9, with the exception of slightly different weights of sec-butyl lithium and styrene and isoprene monomers. The resulting sequentially polymerized linear SIS polymers had styrene contents and molecular weights as described in Table 1.

EXAMPLE 13

To a 5-gallon stirred reactor under a nitrogen atmosphere were added 12.4 kg of cyclohexane solvent and 244.2 g of a 0.125 M solution of sec-butyl lithium in cyclohexane. The temperature of the reactor was brought to 75° C. and 597.1 g of styrene monomer was added. Polymerization of the styrene was allowed to continue for 50 min. The reaction mixture was cooled to 59° C. and 1427.0 g of isoprene monomer was added. The isoprene was allowed to polymerize for 80 minutes, during which the reaction temperature reached a maximum of 92.8° C. At the end of the 80 minutes, the temperature had dropped to 50° C. and 37.7 g of a 1.065 M solution of dibromoethane coupling agent in cyclohexane was added to the reactor. The coupling reaction was allowed to continue for 40 minutes before being terminated by the addition of an excess of isopropanol to the polymer solution. Following the addition of an antioxidant package consisting of a hindered phenol and tris-nonylphenylphosphite (TNPP), the polymer was recovered from solution by devolatilization in a vacuum oven under nitrogen at 100° C. for 3 hrs. The resulting coupled linear SIS polymer had a styrene content of 30.2 wt % and a molecular weight (corrected for composition) of 149,240. The product also contained 17.6 wt % of residual uncoupled SI diblock.

EXAMPLE 14

Example 14 is a sequentially polymerized linear SIS polymer that is commercially available from DEXCO Polymers. The properties are described in Table 1. This SIS polymer is representative of the types employed in the formulations described in U.S. Pat. Nos. 5,143,968 and 5,149,741.

EXAMPLE 15

Example 15 is a linear coupled SIS product that is commercially available from Shell Chemical.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

TABLE 1

LOW RUBBER HMA FORMULATIONS

| EXAMPLE | RUBBER | TYPE | % Sty | CORR PK MW | PS MW | % DIBLOCK | HMA % RUBBER | HMA SAFT (C) | HMA PEEL PE (lb/in) | HMA VISC 130C (cps) | HMA PEAK TENSILE (psi) |
|---|---|---|---|---|---|---|---|---|---|---|---|
| 1 | 6344-18 | SBS | 31.1 | 124,702 | 19375 | 0 | 11 | 60.1 | 4.5 | 9,000 | 101 |
| 2 | 6344-16 | SBS | 31.0 | 117,769 | 18135 | 0 | 11 | 60.1 | 4.2 | 7,250 | 92 |
| 3 | 6504-55 | SBS/SB | 30.1 | 125,180 | 18840 | 21.3 | 11 | 54.9 | 2.4 | 4,375 | 32 |
| 4 | VECTOR 8508* | SBS | 29.4 | 72,500 | 10658 | 0 | 11 | 41.5 | 3.9 | 1,835 | 27 |
| 5 | VECTOR 2518* | SBS | 30.8 | 100,000 | 15400 | 0 | 11 | 55.0 | 4.6 | 5,125 | 72 |
| 6 | Stereon 840A | SBS | 43.8 | 77,000 | 16863 | 0 | 11 | 47.3 | 2.2 | 1,800 | 33 |
| 7 | KRATON 4158** | (SB)$_n$ Radical | 30.0 | 287,492 | 21562 | 17 | 11 | 60.5 | 5.5 | 14,000 | 67 |
| 8 | Stereon 840A*** | SBS | 43.8 | 77,000 | 16863 | 0 | 20 | 56.8 | 1.2 | 7,840 | 95 |
| 9 | 6504.49 | SIS | 30.8 | 120,000 | 18480 | 0 | 11 | 54.5 | 4.8 | 1,825 | 58 |
| 10 | 6504.48 | SIS | 29.9 | 132,591 | 19822 | 0 | 11 | 57.5 | 3.7 | 2,375 | 74 |
| 11 | 6504.47 | SIS | 30.4 | 137,504 | 20901 | 0 | 11 | 58.4 | 4.8 | 2,625 | 67 |
| 12 | 6504.46 | SIS | 30.8 | 159,401 | 24548 | 0 | 11 | 61.3 | 5.3 | 4,500 | 70 |
| 13 | 6504.54 | SIS/SI | 30.2 | 149,237 | 22535 | 17.6 | 11 | 54.3 | 2.6 | 1,850 | 37 |
| 14 | VECTOR 4211* | SIS | 29.5 | 87,754 | 12944 | 0 | 11 | 51.1 | 4.6 | 1,372 | 52 |
| 15 | KRATON 1111** | SIS/SI | 22.0 | 147,000 | 16170 | 16 | 11 | 52.8 | 5.2 | 2,375 | 29 |

*VECTOR is a registered trademark of DEXCO Polymers
**KRATON is a registered trademark of Shell Chemicals
***Stereon is a registered trademark of Firestone Rubber Company

What is claimed as invention is:

1. A hot-melt adhesive composition suitable for disposable goods and wherein the hot melt construction adhesive is applied to a polyolefin or nonwoven substrate by extrusion, spray or multi-line type techniques to be operable to bind at least one elastic, polyolefin, foam, polyethylene, polypropylene, or nonwoven layer to the substrate, the hot melt construction adhesive comprising:
   a) about 5 percent to about 15 percent based on the weight of the hot melt adhesive composition, of a linear A—B—A block copolymer wherein the B component is polyisoprene, the A component is polystyrene, the average peak molecular weight corrected for the composition and the polymer, of a polystyrene block is a minimum of 18,000, the overall average peak molecular weight corrected for the composition of the polymer, of the linear block copolymer ranges from about 120,000 to about 200,000, the A component is present in an amount of about 25 parts to about 35 parts per 100 parts by weight of the block copolymer;
   b) from about 45 percent to about 85 percent of a compatible solid tackifying resin, based on the weight of the hot melt composition;
   c) from about 0 percent to about 35 percent of a plasticizing oil or liquid tackifying resin, based upon the weight of the hot melt adhesive; and
   wherein the A—B—A block copolymer contains less than 5% residual A—B diblock.

2. The hot-melt adhesive composition of claim 1 wherein the linear A—B——A block copolymer is about 8 percent to about 13 percent based on the weight of the hot-melt adhesive.

3. The hot-melt adhesive composition of claim 1 wherein the average molecular weight, corrected for the composition of the polymer, of a polystyrene block ranges from about 18,000 to about 22,000.

4. The hot-melt adhesive composition of claim 1 wherein the average molecular weight, corrected for the composition of the polymer, of the linear A—B—A block copolymer ranges from about 125,000 to about 150,000.

5. The hot-melt adhesive composition of claim 1 wherein the A component is present in an amount of about 28 to about 32 parts per 100 by weight of the A—B—A block copolymer.

6. The hot-melt adhesive of claim 1 wherein the A—B—A block copolymer is produced in a coupling process with the coupling efficiency greater than 95%.

7. The hot-melt adhesive of claim 1 wherein the A—B—A block copolymer is sequentially polymerized resulting in a residual A—B diblock level of less than about 2 percent.

8. A hot-melt adhesive composition suitable for disposable goods and wherein the hot melt construction adhesive is applied to a polyolefin or nonwoven substrate by extrusion, spray or multi-line type techniques to be operable to bind at least one elastic, polyolefin, foam, polyethylene, polypropylene, or nonwoven layer to the substrate, the hot melt construction adhesive comprising:
   a) about 5 percent to about 15 percent based on the weight of the hot melt adhesive composition, of a linear A—B—A block copolymer wherein the B component is polybutadiene, the A component is polystyrene, the average peak molecular weight, corrected for the composition of the polymer, of a polystyrene block is a minimum of 18,000, the overall average peak molecular weight, corrected for the composition of the polymer, of the linear block copolymer ranges from about 100,000 to about 180,000, and wherein the A component is present in an amount of about 25 parts to about 35 parts per 100 parts by weight of the block copolymer;
   b) from about 45 percent to about 85 percent of a compatible solid tackifying resin, based on the weight of the hot melt composition; and
   c) from about 0 percent to about 35 percent of a plasticizing oil or liquid tackifying resin, based upon the weight of the hot melt adhesive.

9. The hot-melt adhesive of claim 8 wherein the linear A—B—A block copolymer is about 8 percent to 13 percent, based on the weight of the hot melt adhesive.

10. The hot-melt adhesive composition of claim 8 wherein the average molecular weight, corrected for the composition of the polymer, of a polystyrene block ranges from about 18,000 to about 22,000.

11. The hot-melt adhesive composition of claim 8 wherein the average molecular weight, corrected for the composition of the polymer, of the linear A—B—A block copolymer ranges from about 110,000 to about 140,000.

12. The hot-melt adhesive composition of claim 8 wherein the A component is present in an amount of about 28 to about 32 parts per 100 by weight of the block copolymer.

13. The hot-melt adhesive composition of claim 8 wherein the A—B—A block copolymer contains less than 5% residual A—B diblock.

14. The hot-melt adhesive composition of claim 8 wherein the A—B—A block copolymer is produced in a coupling process with the coupling efficiency greater than 95%.

15. The hot-melt adhesive of claim 8 wherein the A—B—A block copolymer is sequentially polymerized resulting in a residual A—B diblock level of less than about 2 percent.

* * * * *

UNITED STATES PATENT AND TRADEMARK OFFICE
CERTIFICATE OF CORRECTION

PATENT NO. : 5,750,623
DATED : May 12, 1998
INVENTOR(S) : Charles F. Diehl, et al.

It is certified that error appears in the above-indentified patent and that said Letters Patent is hereby corrected as shown below:

TITLE PAGE, ADD THE FOLLOWING:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 0 | 2 | 4 | 3 | 1 | 2 | 17 May 1977 | Korpman | | | |

FOREIGN PATENT OR PUBLISHED FOREIGN PATENT APPLICATION

| | | DOCUMENT NUMBER | | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|---|
| | WO | 9 | 1 | 0 | 2 | 0 | 3 | 9 A | 21 February 1991 | PCT | | | | |
| | EP | 0 | 5 | 2 | 5 | 9 | 0 | 5 A | February 1993 | Europe | | | | |
| | EP | 0 | 1 | 0 | 4 | 0 | 0 | 5 A | 28 March 1984 | Europe | | | | |
| | EP | 0 | 4 | 5 | 1 | 9 | 1 | 9 A | 16 October 1991 | Europe | | | | |
| | WO | 9 | 5 | 1 | 4 | 0 | 4 | 9 A | 26 May 1995 | PCT | | | | |
| | EP | 0 | 6 | 1 | 1 | 5 | 7 | 5 A | 24 August 1994 | Europe | | | | |

Signed and Sealed this

Twenty-sixth Day of October, 1999

Attest:

Attesting Officer

Q. TODD DICKINSON

Acting Commissioner of Patents and Trademarks